United States Patent [19]
Hughes

[11] Patent Number: 5,499,983
[45] Date of Patent: Mar. 19, 1996

[54] VARIABLE ANGLE SPINAL SCREW

[75] Inventor: Dean Hughes, Cordova, Tenn.

[73] Assignee: Smith & Nephew Richards, Inc., Memphis, Tenn.

[21] Appl. No.: 200,635

[22] Filed: Feb. 23, 1994

[51] Int. Cl.⁶ .......................... A61B 17/70; A61B 17/86
[52] U.S. Cl. ...................... 606/61; 606/73; 403/298
[58] Field of Search ........................ 606/61, 72, 73; 403/298, 292, 356, 318

[56] References Cited

U.S. PATENT DOCUMENTS

| | | | |
|---|---|---|---|
| 3,343,612 | 9/1967 | Flowers | 403/356 |
| 4,569,338 | 2/1986 | Edwards. | |
| 4,987,892 | 1/1991 | Krag et al. | 606/61 |
| 5,053,034 | 10/1991 | Olerud. | |
| 5,176,678 | 1/1993 | Tsou. | |
| 5,209,752 | 5/1993 | Ashman et al. | |
| 5,254,118 | 10/1993 | Mirkovic. | |
| 5,282,801 | 2/1994 | Sherman. | |

Primary Examiner—Stephen C. Pellegrino
Assistant Examiner—Scott B. Markow
Attorney, Agent, or Firm—Pravel, Hewitt, Kimball & Krieger

[57] ABSTRACT

A spinal fastening apparatus for use in spinal fixation systems, comprising a bone screw, a collar and a locking pin. The bone screw has a threaded shaft portion with a generally longitudinal axis and a head portion having an eyelet with a central bore. The collar is generally U-shaped with a transverse axis and a slot adapted for placement over the eyelet portion of the screw. The elongated locking pin has an outer surface with gripping means on at least a portion of the outer surface and is sized and shaped to be slidably inserted through the eyelet. Surface portions of the collar and eyelet each include means for engaging the gripping means of the pin when the pin is inserted through the eyelet bore and the eyelet occupies the slot of the collar. The collar is capable of pivoting in relation to the eyelet to adjust for angulation between the longitudinal axis of the threaded shaft and the transverse axis of the collar and being locked into a selected angled position.

21 Claims, 4 Drawing Sheets

VARIABLE ANGLE SPINAL SCREW

FIELD OF THE INVENTION

The present invention relates to spinal fixation systems for use in the treatment of spinal deformities and more particularly to an apparatus for fixing a stabilizing appliance to spinal vertebrae.

BACKGROUND OF THE INVENTION

Spinal fusion, especially in the lumbar and sacral region is regularly used to correct and stabilize spinal curves and to stabilize the lumbar and sacral spine temporarily while solid spinal fusions develop in the treatment of other spinal abnormalities. A spinal rod system is one of the stabilization systems currently in use. In spinal rod systems, elongated rods are used to bridge across various portions of the spine. Bone screws and coupling devices are used to attach the rods to various portions of the spinal vertebrae. In some situations one end of the elongated rod is anchored in the sacral region of the spine with the other end being anchored in a selected lumbar vertebrae.

When spinal rod systems are anchored in the sacral region, the ability to achieve strong sacral fixation between the sacral and lumbar vertebrae becomes difficult. The anatomical position of the sacrum can cause a 30° or more difference between the angle of implantation of bone screws in the sacral and lumbar vertebrae. When the spinal rod is not properly contoured to a patient's lordotic curve, misalignment occurs between the implanted bone screws and the coupling devices which causes inadequate fixation of the spinal system.

A spinal rod system currently in use is shown in U.S. Pat. No. 5,102,412 to Rogozinski. In the Rogozinski Spinal System, two elongated rods are used with cross-bars extending laterally between the rods to form a quadrilateral construct. Hooks, bone screws or a combination of hooks and screws are attached to the vertebrae, and U-shaped couplers are used to secure the hooks or screws to the spinal rods. The bone screws each have a T-shaped head which is pivotally received in a coupler. The coupler has a U-shaped open back with a recess for receiving either the T-head of the screw or the spinal rod. The bottom of the coupler has an opening for receiving the threaded shank of the T-screw with the screw head fitting between the side walls of the coupler. The side walls also include aligned openings for receiving an elongate bar that extends through the aligned openings in a direction transverse to the recess. The bar has set screws for holding the T-screw and spinal rod in place in the coupler. Couplers are connected to each other through the elongate bar.

When a spinal rod system such as the Rogozinski spinal system is implanted in the sacral region of the spine, a need exists for a bone screw which allows for the variability in angulation found between the sacral and lumbar vertebrae.

A need also exists for bone screws having the ability to pivot in the medial/lateral plane as well as the ability to pivot and lock in the cephalad/caudal plane while maintaining the proper alignment between an implanted bone screw, a coupler and a rod of a spinal fixation system.

SUMMARY OF THE INVENTION

It is thus an object of the present invention to provide a fastening apparatus for use in spinal rod systems that allows for angulation in both the medial/lateral and the cephalad/caudal plane of the human body and can then be locked into the selected angular position. The fastening apparatus of the present invention includes a bone screw, a collar and a locking pin. The bone screw has a threaded shaft portion configured to be surgically implanted into a patient's bone tissue and a head portion with an eyelet having a central bore.

The generally U-shaped collar has a transverse axis and a slot that is placed over the eyelet portion of the screw. The elongated locking pin has longitudinal grooves on at least a portion of the outer surface and is sized and shaped to be slidably inserted through the eyelet bore. Surface portions of the collar and the eyelet include regularly spaced teeth, sized and shaped to engage with the grooves on the pin when the pin is inserted through the eyelet bore and the eyelet occupies the slot of the collar.

When the fastening apparatus is assembled the collar is capable of pivoting in relation to the eyelet to adjust for angulation between the longitudinal axis of the threaded shaft and the transverse axis of the collar. The pin grooves and teeth on the surfaces of the eyelet bore and collar engage with each other for locking the collar into a selected angled position. The collar allows for angulation of the fixation apparatus in a range of 140° in the medial/lateral plane and a range of 64° in the cephalad/caudal plane.

In a preferred embodiment, the fastening apparatus of the present invention is used in the sacrum of a patient in order to maintain the coronal plane angulation in spinal rod systems that have an attachment from the sacrum to the lumbar vertebrae.

BRIEF DESCRIPTION OF THE DRAWINGS

A better understanding of the invention can be obtained when the detailed description of the exemplary embodiments set forth below is reviewed in conjunction with the accompanying drawings, in which:

FIG. 1A is a top plan view of the assembled apparatus of FIG. 1;

FIG. 1B is a fragmentary side plan view of the assembled apparatus of FIG. 1;

DETAILED DESCRIPTION OF PREFERRED EMBODIMENT

Figure 1:
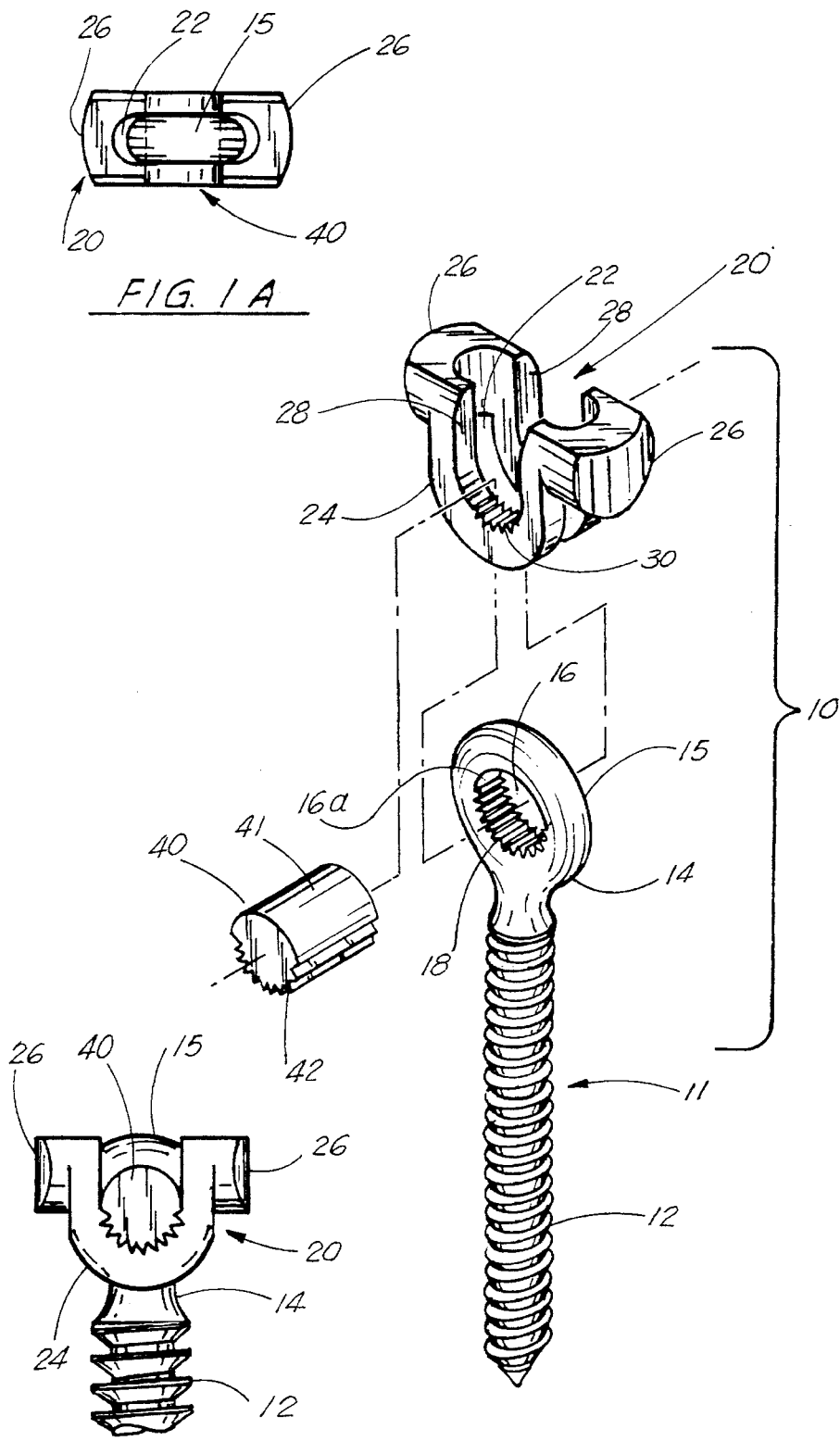
FIG. 1 is a perspective exploded view of the preferred embodiment of the apparatus of the present invention.
Figure 2:
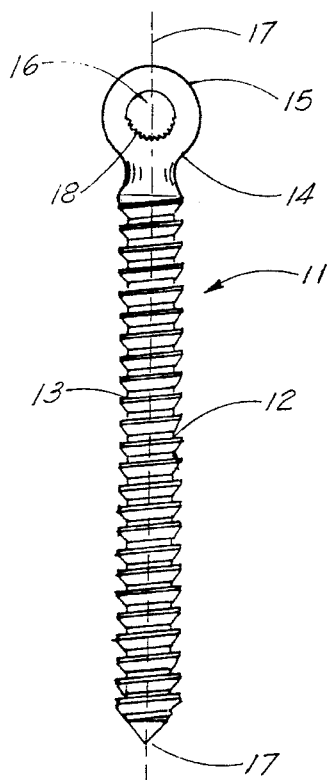
FIG. 2 is a side plan view of the bone screw of the apparatus of the present invention.
Figure 3:
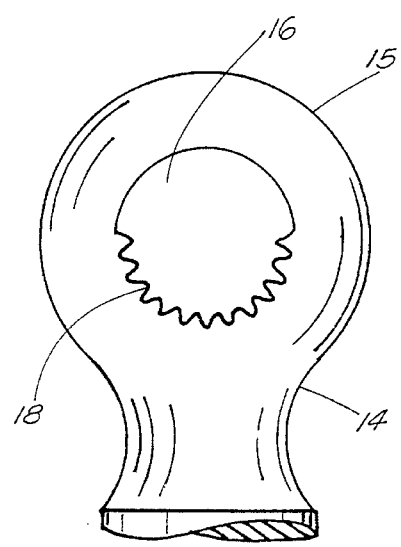
FIG. 3 is an enlarged view of a portion of the bone screw of FIG. 2.
Figure 4:
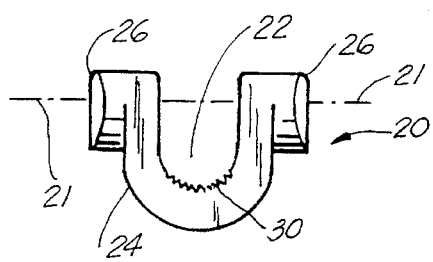
FIG. 4 is a side plan view of the collar of the apparatus of the present invention.
Figure 5:
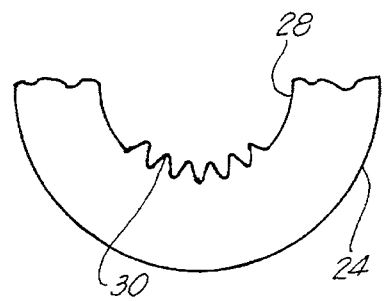
FIG. 5 is an enlarged fragmentary view of the collar of FIG. 4.
Figure 6:
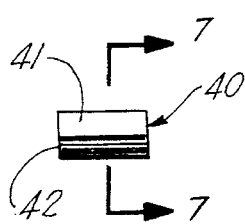
FIG. 6 is a side plan view of the locking pin of the apparatus of the present invention.
Figure 7:
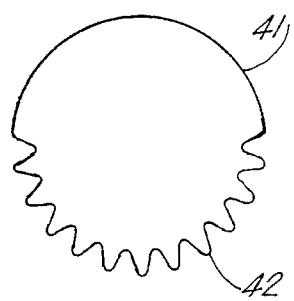
FIG. 7 is an enlarged cross-sectional view looking along the site line 7—7 of FIG. 6.

FIG. 1 illustrates the preferred embodiment of the fixation apparatus of the present invention designated generally by the numeral 10. The fixation apparatus 10 includes a bone screw 11, a collar 20 and an elongated locking pin 40. Bone screw 11 has a longitudinal axis 17 and a shank portion 12 with a bone engaging course thread 13 thereon which allows it to be surgically implanted into a patient's bone tissue, and in the preferred embodiment either lumbar or sacral vertebrae (FIGS. 1 and 2). A head portion 14 has an eyelet 15 with a central bore 16 (FIGS. 1 and 2). Bore 16 has a surface 16a with a portion of bore surface 16a being textured, preferably at least 30%. In the preferred embodiment the textured surface is formed from regularly spaced teeth 18 as shown in FIGS. 1 and 3.

Collar 20 is generally U-shaped with a transverse axis 21 and a centrally located slot 22 sized and shaped for placing over the eyelet 15 of the screw 11 (FIGS. 1, 1a, 1b and 4). Collar 20 includes a middle U-shaped portion 24 and extending end portions 26 with the slot 22 positioned in the middle U-shaped portion 24. As shown in FIG. 1, the middle portion 24 includes inner walls 28 with flat surfaces on either side of the slot 22. A portion of the flat surface of each of the inner walls 28 is textured, preferably at least 30% of the surface 28. In the preferred embodiment the textured surface is comprised of regularly spaced teeth 30 which match and intermesh the regularly spaced teeth 18 on the bore surface 16a of eyelet 15.

The elongated locking pin 40 is generally cylindrical in shape and is sized and shaped to be inserted through the eyelet bore 16 (FIG. 1b). Locking pin 40 has an outer surface 41 with a portion of the outer surface 41 being textured to provide a gripping surface. In the preferred embodiment the textured surface includes regularly spaced longitudinal grooves 42, preferably over at least 30% of the outer surface 41. The longitudinal grooves 42 of the locking pin 40 are sized and shaped to engage or intermesh with the teeth 18 on the bore surface 16a and the teeth 30 on the inner wall surfaces 28 of the collar 20 (FIG. 1b). The teeth 30 are aligned on the wall surfaces 28 and the grooves 42 are aligned on the pin surface 41 so as to allow for locking the collar 20 in spaced increments of between about 10° to 20°.

Figure 8:
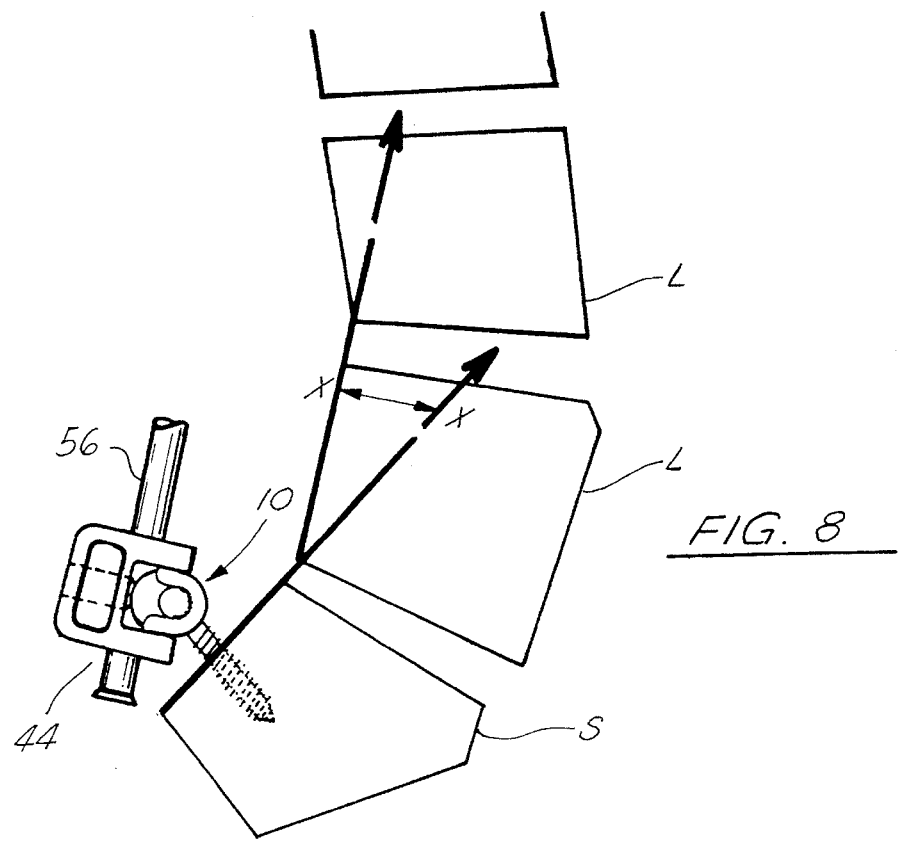
FIG. 8 is a schematic side view of a partial spinal column with an implanted fixation apparatus of the present invention attached to a portion of spinal rod system.

The fixation apparatus 10 of the present invention is used in combination with a spinal rod system and is an improvement on the bone screws presently in use. In one preferred embodiment the apparatus is used with a Rogozinski Spinal System in which couplers are utilized to make the connection between the vertebrae and the spinal rods. The Rogozinski Spinal System is described in U.S. Pat. No. 5,102,412 and sold by Smith & Nephew Spine. The fixation apparatus 10 of the present invention accommodates the difference in angulation found between the sacral vertebrae S and lumbar vertebrae L, as illustrated in FIG. 8, where a difference of angulation defined as X—X, can be approximately 30°.

Figure 9:
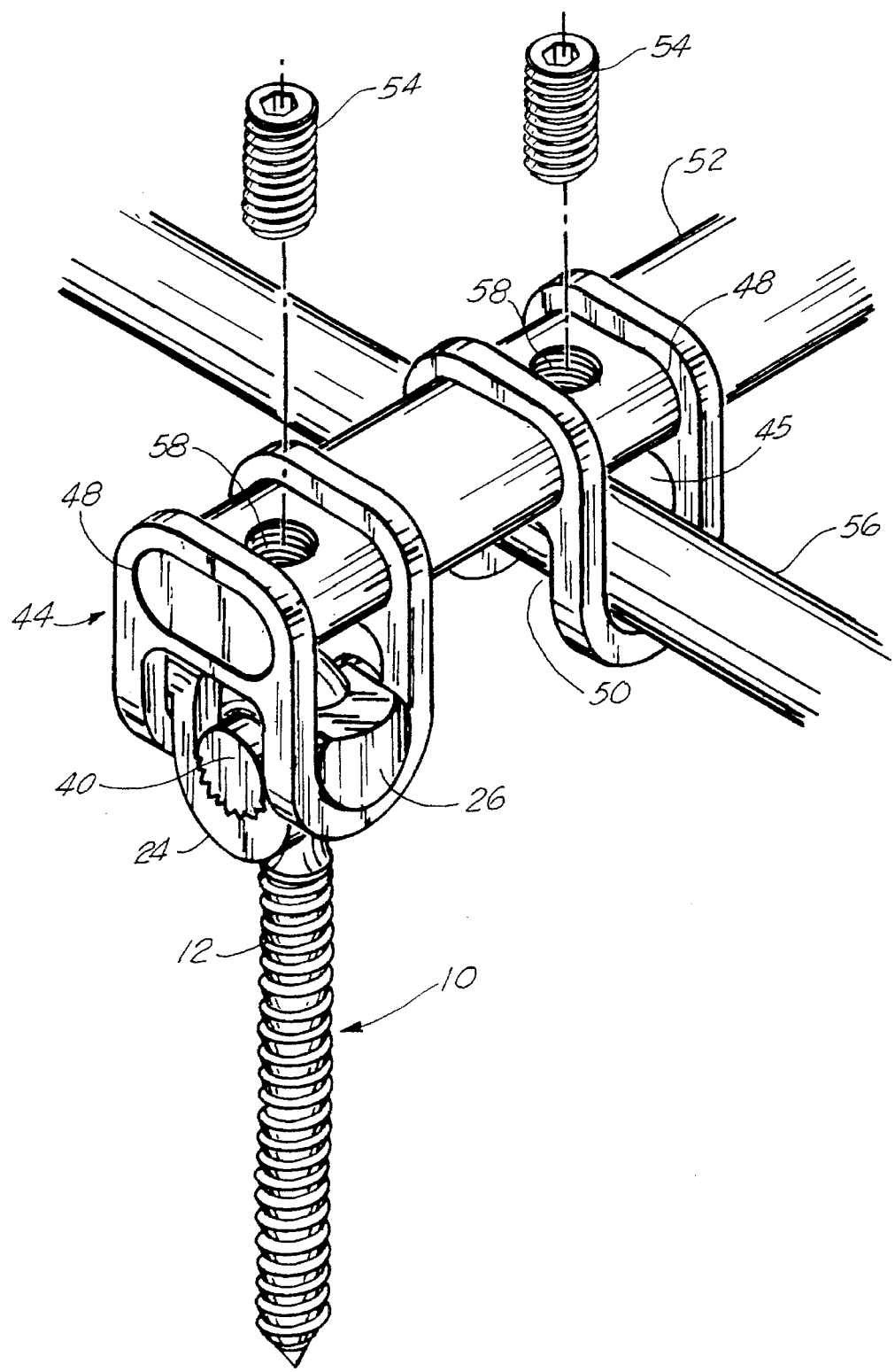
FIG. 9 is a perspective exploded view of the present invention is use with a portion of a spinal rod system.
Figure 10:
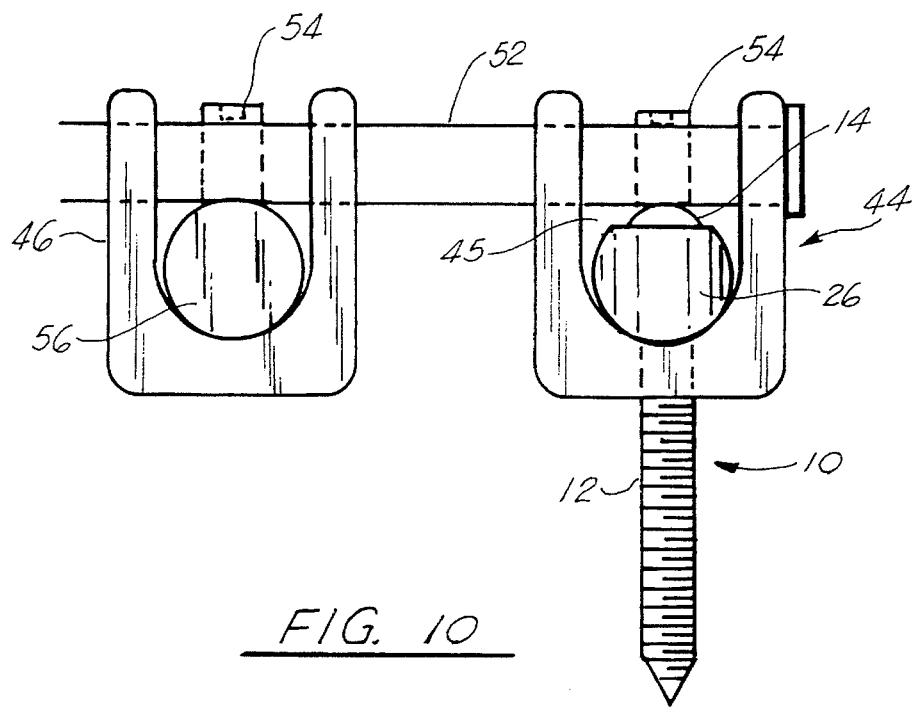
FIG. 10 is a side plan view of the fixation apparatus of the present invention secured in a coupler of a spinal rod system.

A spinal system such as the Rogozinski Spinal System is illustrated in FIGS. 9 and 10, where a coupler 44 has a U-shaped open back with aligned side walls 46 and a recess 45 between them for receiving a T-screw. An opening 50 is in the bottom of the coupler 44 for receiving the threaded shank of a T-screw with the screw head fitting between the side walls of the coupler 44.

The fixation apparatus 10 is pre-assembled such that the collar 20 is placed over the eyelet 15 of the bone screw 11 with the eyelet 15 extending through the slot 22 of the collar 20. The pin 40 is inserted through the eyelet bore 16 with the pin grooves 42 engaging with the teeth 18 on the bore surface 16a and the pin 40 extending out from both sides of the eyelet bore 16 (FIG. 1b). At this pre-assembled stage, the collar 20 is capable of pivoting up and down in a cephalad/caudal plane of the human body or pivoting from side to side in relation to the longitudinal axis 17 of the bone screw 11 (FIG. 1b). The preassembled fixation apparatus 10 is inserted into the coupler 44 with the collar 20 resting in the recess 45 between the side walls 46 and the threaded shank 12 extending through the opening 50. The threaded shank portion 12 of the bone screw 11 is then implanted into a patient's vertebrae.

The extending end portions 26 of the collar 20 allow the bone screw 11 to pivot side to side in the coupler 44, in a plane which passes through the longitudinal axis 17 of the bone screw or the medial/lateral plane of the body in relation to the longitudinal axis of the bone screw 11, within a range of generally 140°. The collar 20 is also capable of pivoting from side to side in relation to the eyelet 15 to adjust for angulation between the longitudinal axis 17 of the implanted bone screw 11 and the transverse axis 21 of the collar 20. The adjustability of this angulation is a range of generally 64° in the a plane which intersects the transverse axis 21 of the collar 20 or the cephalad/caudal plane of the body.

An elongated bar 52 is inserted through the aligned openings 48 in the side walls 46 of the coupler 44 holding the apparatus 10 to connect it with a second coupler 44 holding a spinal rod 56 (FIG. 9). After the spinal rod system has been completely or partially installed and adjusted for angulation and alignment set screws 54 are inserted into openings 58 in the elongated bar 52 in order to tighten the assembly. The tightening of the set screw 54 pushes down on the screw head 14 and causes the collar 20 to pull up via the coupler's 44 upward force enabling the teeth 30 on the collar 20 to engage with the pin grooves 42 on the pin 40 extending through the eyelet bore 16 to provide a locking means for the apparatus 10. The collar teeth 30 and pin grooves 42 engage with each other and lock the collar 20 into a selected angled position within a range of 64° (FIG. 10). In a preferred embodiment, the apparatus 10 is formed from stainless steel or other biocompatible material.

The apparatus 10 of the present invention allows for angulation in two planes—the medial/lateral and cephalad/caudal plane. The intermeshing teeth 18 of the eyelet 14, the teeth 30 of the collar 20 and the grooves 42 of the pin 40 provide a locking mechanism or locking means that resists the rotational movement imposed during in vivo loading conditions in the cephalad/caudal plane with an implanted spinal system.

It should be understood that there can be improvements and modifications made to the embodiments of the invention described in detail above without departing from the spirit or scope of the invention, as set forth in the accompanying claims.

What is claimed is:

1. A spinal fastening apparatus for use in spinal fixation systems, comprising:

a) a bone screw with a threaded shaft portion having a generally longitudinal axis and configured to be surgically implanted into a patient's bone tissue and a head portion extending above the patient's bone tissue when the shaft is implanted;

b) the head portion having an eyelet with a central bore;

c) a generally U-shaped collar having a transverse axis and a slot adapted for placement over the eyelet portion of the screw, with a U-shaped portion of the collar being in the middle and including extending end portions with the slot being positioned in the middle portion;

d) an elongated locking pin having an outer surface with a gripping portion on at least part of the outer surface, said pin sized and shaped to be slidably inserted through the eyelet;

e) surface portions of the collar and eyelet each including means for engaging the gripping portion of the pin when the pin is inserted through the eyelet bore and the surface portions of the collar when the eyelet occupies the slot of the collar;

f) said engaging means and gripping portion having intermeshing surfaces that include textured surface portions of the collar and the eyelet;

g) the generally U-shaped collar allowing for pivoting of the collar from side to side in relation to the eyelet of the bone screw for adjustment of the angulation between the longitudinal axis of the threaded shaft of the bone screw and the transverse axis of the collar when the spinal fastening apparatus is implanted into a patient's bone tissue and attached to a spinal fixation system;

h) wherein said intermeshing surfaces of the engaging means and gripping portion lock the collar and bone screw together into a selected angled position when the pin is inserted through the eyelet of the head portion and the collar when the eyelet occupies the slot of the collar.

2. The apparatus of claim 1, wherein the gripping portion on the locking pin includes regularly spaced longitudinal grooves placed on at least a portion of the outer surface.

3. The apparatus of claim 2, wherein the longitudinal grooves cover at least 30% of the outer surface of the locking pin.

4. The apparatus of claim 1, wherein the textured surface portions of the collar and eyelet include regularly spaced teeth sized and shaped to lock with the gripping means of the pin.

5. The apparatus of claim 1, wherein the textured surface portion of the collar is on a surface of the U-shaped middle portion of the collar.

6. The apparatus of claim 1, wherein the textured surface portion of the eyelet is on a surface of the central bore.

7. The apparatus of claim 6, wherein the textured surface of the bore includes at least 30% of the bore's surface.

8. The apparatus of claim 1, and further including a generally U-shaped open backed coupler with aligned side walls, a recess between the side walls and an opening in a bottom portion of the coupler for receiving the threaded shank of the bone screw, the collar includes extending end portions shaped for placement in the coupler recess with the threaded shank extending through the bottom opening of the coupler, said collar end portions shaped to allow for side to side pivoting of the collar when the collar is placed in the coupler, wherein said pivoting allows for angulation of the apparatus of a range of generally 140° in a plane which passes through the longitudinal axis of the threaded shaft of the bone screw.

9. The apparatus of claim 1, wherein the pivoting of the collar from side to side in relation to the eyelet of the bone screw allows for angulation between the longitudinal axis of the threaded shaft of the bone screw and the transverse axis of the collar of a range of generally 64° in a plane which intersects the transverse axis of the collar.

10. A spinal fastening apparatus for use in spinal fixation systems, comprising:

a) a bone screw with a threaded shaft portion having a generally longitudinal axis and configured to be surgically implanted into a patient's bone tissue and a head portion extending above the patient's bone tissue when the shaft is implanted;

b) the head portion having an eyelet with a central bore;

c) a generally U-shaped collar having a transverse axis, a middle U-shaped portion and extending end portions with a slot positioned in the middle portion, said slot adapted for placement over the eyelet portion of the screw;

d) an elongated locking pin having an outer surface with regularly spaced longitudinal grooves on at least a portion of the outer surface, said pin sized and shaped to be slidably inserted through the eyelet;

e) surface portions of the collar U-shaped middle portion and eyelet each including textured portions for engaging the longitudinal grooves of the pin when the pin is inserted through the eyelet bore and the U-shaped middle portion of the collar when the eyelet occupies the slot of the collar;

f) said textures surface portions of the collar and the eyelet include regularly spaced teeth sized and shaped to engage with the grooves on the pin;

g) the collar allowing for pivoting of the collar from side to side in relation to the eyelet of the bone screw for adjustment of the angulation between the longitudinal axis of the threaded shaft of the bone screw and the transverse axis of the collar when the spinal fastening apparatus is implanted into a patient's bone tissue and attached to a spinal fixation system;

h) wherein the pin grooves and teeth on the surfaces of the eyelet bore and collar engage with each other for locking the collar and bone screw together into a selected angled position when the pin is inserted through the eyelet of the head portion and the collar when the eyelet occupies the slot of the collar.

11. The apparatus of claim 10, wherein the longitudinal grooves of the locking pin cover at least 30% of the outer surface of the pin.

12. The apparatus of claim 10, wherein the textured surface portion of the eyelet is on a surface of the central bore.

13. The apparatus of claim 12, wherein the textured surface of the bore includes at least 30% of the bore's surface.

14. The apparatus of claim 10, and further including a generally U-shaped open backed coupler with aligned side walls, a recess between the side walls and an opening in a bottom portion of the coupler for receiving the threaded shank of the bone screw, the collar includes extending end portions shaped for placement in the coupler recess with the threaded shank extending through the bottom opening of the coupler, said collar end portions shaped to allow for side to side pivoting of the collar when the collar is placed in the coupler, wherein said pivoting allows for angulation of the apparatus of a range of generally 140° in a plane which passes through the longitudinal axis of the threaded shaft of the bone screw.

15. The apparatus of claim 10, wherein the pivoting of the collar from side to side in relation to the eyelet of the bone screw allows for angulation between the longitudinal axis of the threaded shaft of the bone screw and the transverse axis of the collar of a range of generally 64° in a plane which intersects the transverse axis of the collar.

16. A spinal fastening apparatus for use in spinal fixation systems, comprising:

a) a bone screw with a threaded shaft portion having a generally longitudinal axis and configured to be surgically implanted into a patient's bone tissue and a head portion extending above the patient's bone tissue when the shaft is implanted;

b) the head portion having an eyelet with a central bore;

c) a generally U-shaped collar having a transverse axis and a slot adapted for placement over the eyelet portion of the screw, said collar including a middle U-shaped portion and extending end portions with the slot positioned in the middle portion;

d) an elongated locking pin having an outer surface with regularly spaced longitudinal grooves on at least a portion of the outer surface, said pin sized and shaped to be slidably inserted through the eyelet bore;

e) surface portions of the U-shaped middle portion of the collar and the central bore of the eyelet each including textured portions for engaging the longitudinal grooves of the pin when the pin is inserted through the eyelet bore and the U-shaped middle portion of the collar when the eyelet occupies the slot of the collar;

f) said textures surface portions of the collar and the eyelet include regularly spaced teeth sized and shaped to engage with the grooves on the pin;

g) the generally U-shaped collar allowing for pivoting of the collar from side to side in relation to the eyelet of the bone screw for adjustment of the angulation between the longitudinal axis of the threaded shaft of the bone screw and the transverse axis of the collar;

h) wherein the pin grooves and teeth on the surfaces of the eyelet bore and collar engage with each other for locking the collar and the bone screw together into a selected angled position when the pin is inserted through the eyelet of the head portion and the collar when the eyelet occupies the slot of the collar.

17. The apparatus of claim 16, wherein the longitudinal grooves of the locking pin cover at least 30% of the outer surface of the pin.

18. The apparatus of claim 16, wherein the textured surface of the eyelet bore includes at least 30% of the bore's surface.

19. The apparatus of claim 10, and further including a generally U-shaped open backed coupler with aligned side walls, a recess between the side walls and an opening in a bottom portion of the coupler for receiving the threaded shank of the bone screw, the collar includes extending end portions shaped for placement in the coupler recess with the threaded shank extending through the bottom opening of the coupler, said collar end portions shaped to allow for side to side pivoting of the collar when the collar is placed in the coupler, wherein said pivoting allows for angulation of the apparatus of a range of generally 140° in a plane which passes through the longitudinal axis of the threaded shaft of the bone screw.

20. The apparatus of claim 16, wherein the pivoting of the collar from side to side in relation to the eyelet of the bone screw allows for angulation between the longitudinal axis of the threaded shaft of the bone screw and the transverse axis of the collar of a range of generally 64° in a plane which intersects the transverse axis of the collar.

21. A spinal fastening apparatus for use in spinal fixation systems, comprising:

a) an elongated bone screw with (i) a threaded shaft portion configured to be surgically implanted into a patient's bone tissue and (ii) a head extending above the patient's bone tissue when the shaft is implanted;

b) The head including a bore extending therethrough;

c) holding means for holding the head, said holding means including surface portions positioned on opposite sides of the head aligned with said bore;

d) an elongated locking pin sized and shaped for insertion through said bore and being aligned with said surface portions;

e) the pin and the surface portions of the holding means and bore including cooperating gripping means for gripping each other and holding the bone screw in a fixed position relative to the holding means;

f) the holding means having a middle U-shaped portion and extending end portions with a slot positioned in the middle portion to allow pivoting of the holding means and bone screw relative to each other for adjusting the angulation between the threaded shaft of the bone screw and the holding means; and g) means for holding the pin against the surface portions of the holding means for locking the bone screw relative to the holding means.

* * * * *